United States Patent [19]
Kramer et al.

[11] Patent Number: 6,162,835

[45] Date of Patent: Dec. 19, 2000

[54] STABLE ACTIVE-INGREDIENT COMBINATION FOR THE DISINFECTION AND CLEANING OF CONTACT LENSES, AND PACKING AND PROCESS FOR THE PREPARATION THEREOF

[75] Inventors: Axel Kramer; Peter Rudolph, both of Greifswald; Brigitte Meyer; Hanns Pietsch, both of Hamburg, all of Germany

[73] Assignee: BODE Chemie GmbH & Co., Hamburg, Germany

[21] Appl. No.: 09/349,581

[22] Filed: Jul. 8, 1999

[30] Foreign Application Priority Data

Jul. 23, 1998 [DE] Germany ............................. 198 33 173
Aug. 4, 1998 [DE] Germany ............................. 198 35 064

[51] Int. Cl.[7] ........................... A61K 31/165; C11D 43/00
[52] U.S. Cl. .......................... 514/840; 514/568; 514/553; 510/113; 510/115; 424/498
[58] Field of Search .................................... 514/840, 568, 514/553, 498; 510/113, 115

[56] References Cited

U.S. PATENT DOCUMENTS 4,448,705  5/1984  Gray ......................................... 252/102
5,411,597  5/1995  Tsao et al. ................................ 134/26

FOREIGN PATENT DOCUMENTS 0 096 525  5/1983  European Pat. Off. .
WO 87/01562  3/1987  WIPO .

*Primary Examiner*—James H. Reamer
*Attorney, Agent, or Firm*—Norris McLaughlin & Marcus P.A.

[57] ABSTRACT

Contact-lens disinfectant containing
(a) magnesium monoperphthalate and
(b) sodium cumenesulphonate,
(c) sodium alkylbenzenesulphonate,
(d) isotridecanol ethoxylate and
(e) methylhydroxyethylcellulose,
and packaging and a process for the preparation thereof.

9 Claims, No Drawings

STABLE ACTIVE-INGREDIENT COMBINATION FOR THE DISINFECTION AND CLEANING OF CONTACT LENSES, AND PACKING AND PROCESS FOR THE PREPARATION THEREOF

DESCRIPTION

The present invention relates to an active-ingredient combination based on magnesium monoperphthalate hexahydrate and surfactants for the disinfection and cleaning of contact lenses, and packaging and a process for the preparation thereof.

Contact-lens disinfectants are medical products which, owing to their potential risk, are classified in risk class 2b. Accordingly, the hygiene of contact lenses and therefore also the performance of disinfectants and cleaning agents for contact lenses are subject to high requirements. These relate in particular to the cleaning ability and the microbiological performance, but also to the mucous membrane compatibility of the agents used. Although the prior art discloses a whole series of disinfectants and cleaning agents for contact lenses, most of the agents on the market are unsatisfactory with respect to their disinfection capacity.

The object of the present invention was therefore to overcome the disadvantages of the prior art and to develop disinfectants which are stable, and accordingly are active, for from one to three years in solid form (for example as a powder, granules or the like) and for at least 8 to 12 hours (i.e. overnight) in aqueous solution.

Surprisingly, this object is achieved by contact-lens disinfectants containing
 (a) magnesium monoperphthalate and
 (b) sodium cumenesulphonate,
 (c) sodium alkylbenzenesulphonate,
 (d) isotridecanol ethoxylate and
 (e) methylhydroxyethylcellulose.

Although it is known that monoperphthalates and in particular magnesium monoperphthalate have good microbicidal effectiveness, are tolerated well by the skin, mucous membranes and wounds and have high material compatibility, the prior art has also already disclosed contact-lens disinfectants containing alkaline earth metal salts of monoperphthalic acid. However, the prior art has nevertheless not disclosed the path to the present invention.

Although international patent application WO 87/01562 discloses contact-lens disinfection preparations containing alkaline earth metal salts of monoperphthalic acid, these preparations also contain complexing agents, such as sodium EDTA or alkali metal salts of hexametaphosphate. In a particular embodiment, these preparations are also in the form of granules, in which the active ingredients are coated with binders, such as ethylcellulose, polyglycol or polyvinylpyrrolidone. However, this specification also reveals (cf. Example 1) that aqueous solutions of the active ingredient are stable for less than one hour and therefore do not meet the requirements made, as stated above, of a contact-lens disinfectant.

European patent specification EP 0 096 525 discloses disinfectant compositions comprising a peroxy compound, an alkali metal chloride, surfactants and builders for detergents. However, these preparations are unsuitable for use in the human eye and therefore also in the area of contact-lens care and accordingly are, according to the patent, proposed for the disinfection of articles, but in particular baby diapers.

The contact-lens disinfectants according to the invention are preparations which are satisfactory in every respect and surprisingly offer the advantage over the prior art of being effective for more than 12 hours in aqueous solution. In addition, they are distinguished by excellent tolerability by the skin, mucous membranes and wounds and have high material compatibility.

Preference is given in accordance with the invention to contact-lens disinfectants which are distinguished by the following composition:
 (a) from 70 to 90% by weight of magnesium monoperphthalate,
 (b) from 5 to 15% by weight of sodium cumenesulphonate,
 (c) from 3 to 10% by weight of sodium alkylbenzenesulphonate,
 (d) from 0.5 to 5.0% by weight of isotridecanol ethoxylate 9 EO, and
 (e) from 0.1 to 2.0% by weight of methylhydroxyethylcellulose, in each case based on the total weight of the final product.

The present invention also relates to a process for the preparation of solid active-ingredient concentrates which is characterized in that a spray solution is prepared from sodium cumenesulphonate, methylhydroxyethylcellulose and water and is sprayed onto a mixture of magnesium perphthalate powder and sodium alkylbenzoate powder in a fluidized-bed drier at an air intake temperature of from 60 to 80° C., and in that these granules are coated with a melt of isotridecanol ethoxylate.

It is particularly advantageous in accordance with the invention, in order to prepare solid active-ingredient concentrates, for example in (effervescent) tablet, powder, pellet or granule form, to spray from 70 to 90% by weight of magnesium monoperphthalate hexahydrate with an aqueous solution of from 0.1 to 2.0% by weight of methylhydroxyethylcellulose and from 5 to 15% by weight of sodium cumenesulphonate in a fluidized-bed drier at an air intake temperature of from 60 to 80° C., subsequently to mix from 3 to 10% by weight of sodium alkylbenzenesulphonate with the granules, and to coat this mixture, still in the fluidized-bed drier, with a melt of from 0.5 to 5.0% by weight of isotridecanol ethoxylate 9 EO, the percentages in each case being based on the total weight of the final product.

Screening is used to remove, for example, a particle size of from 50 to 500 $\mu$m. These granules are packed, for example, in portions of from 10 to 500 mg, preferably in portions of from 50 to 200 mg, either in blister packs or gelatin capsules, enabling a use solution to be freshly prepared in each case. At room temperature, the granules are stable for 3 years. For use, a portion is in each case dissolved in water, giving a 0.25 to 1.0% strength by weight aqueous solution of the active-ingredient granules, based on the total weight of this solution. The use solution is stable for about 24 hours.

EXAMPLES

Preparation of stable granules

A solution is prepared from 19.4 parts by weight of sodium cumenesulphonate, 2.56 parts by weight of methylhydroxyethylcellulose and 119.6 parts by weight of water and is adjusted to a pH of from 6.5 to 7.5 using sodium hydroxide solution. This solution is sprayed onto 160 parts by weight of magnesium monoperphthalate hexahydrate in a fluidized-bed drier at an air intake temperature of from 60 to 80° C. 14.8 parts by weight of sodium alkylbenzenesulphonate are mixed with these granules, and this mixture is coated, still in the fluidized-bed drier, with a melt of 3.2 parts by weight of isotridecanol ethoxylate 9 EO. The particle size is determined by the air velocity. Oversized and undersized particles are screened out. The finished granules have an active-oxygen content of from 3.9 to 4.4% (m/m), and the pH of a 0.5% strength by weight aqueous solution is from 5.0 to 5.6.

Stability of the granules

The granules prepared as described above were introduced in portions of 50 mg into rigid PVC blister film and sealed with a laminated polyethylene/aluminium foil. The granules packed in this way were stored at room temperature (22° C.), and the active-oxygen content was measured:

Results: Initial value: 4.09%, after 24 months 3.99%, after 36 months 3.96%

In a further experiment, the same granules were packed in portions of 50 mg in gelatin capsules and stored at 31° C. and 40% relative atmospheric humidity, and the active-oxygen content was measured:

Results: Initial value: 4.16%, after 5 months 3.87%, after 24 months 3.81%, and after 36 months 3.84%.

Stability of a 0.5% strength by weight aqueous solution

The above-described granules based on magnesium monoperphtha(ate hexahydrate were diluted with tap water to give a 0.5% strength by weight aqueous solution, and the active-oxygen content of this "use solution" was determined.

Results: Initial value 0.0021%, after 8 hours at 20° C. 0.0020%, after 12 hours at 20° C. 0.0022%.

Microbicidal effectiveness of a 0.5% strength by weight aqueous solution

A 0.5% strength by weight aqueous solution of the above-described granules based on magnesium monoperphthalate hexahydrate was tested for its microbicidal effectiveness using the quantitative suspension test of the German Society for Hygiene and Microbiology (DGHM). The test microbes used were the following: *Staphylococcus aureus* ATCC 6538, Pseudomonas aeruginosa ATCC 15442 and *Candida albicans* ATCC 10231. The exposure was carried out with 0.2% of albumin, and the deactivation was effected by TLHTh (Tween, lecithin, histidine, thiosulphate) inhibitor.

Results: In all cases, the microbe reduction at 21° C. was more than 4 logarithmic orders, corresponding to greater than 99.99%.

Mucous-membrane toleration of a 0.5% strength by weight aqueous solution

The mucous-membrane toleration was tested on incubated chicken eggs using the HET-CAM test. A 0.5% strength by weight aqueous solution of the above-described granules based on magnesium monoperphthalate is applied to the chorion, and the changes in the vascular system are then assessed.

Results: After 30 sec 0.1a, 1a, 1a, 1a; after 120 sec 1a, 1a, 1a, 1a, 1a, 1b; after 300 sec 1a, 1a, 1a, 1a, 1b, 1c.

Assessment: 0=no reaction, 1a=slight hyperaemia, 1b=moderate hyperaemia, 1c=significant hyperaemia.

Material compatibility of a 0.5% strength by weight aqueous solution

The material compatibility was tested both on hard contact lenses based on silicone rubber and on soft contact lenses based on polyhydroxyethyl methacrylate. 12 hard and 12 soft contact lenses were placed in a 0.5% strength by weight aqueous solution of the above-described granules and stored there for 100 hours at 22° C. The solution was replaced every 10 hours. Haze/clarity and dimensional stability were assessed.

Result: In all cases, there was no haze and no change in the diameter and thickness.

What is claimed is:

1. A contact-lens disinfectant comprising
   (a) magnesium monoperphthalate and
   (b) sodium cumenesulphonate,
   (c) sodium alkylbenzenesulphonate,
   (d) isotridecanol ethoxylate and
   (e) methylhydroxyethylcellulose.

2. The contact-lens disinfectant according to claim 1, comprising, based on the total weight of the final product,
   (a) from about 70 to 90% by weight of magnesium monoperphthalate,
   (b) from about 5 to 15% by weight of sodium cumenesulphonate,
   (c) from about 3 to 10% by weight of sodium alkylbenzenesulphonate,
   (d) from about 0.5 to 5.0% by weight of isotridecanol ethoxylate 9 EO, and
   (e) from about 0.1 to 2.0% by weight of methylhydroxyethylcellulose.

3. The contact-lens disinfectant according to claim 1 in the form of granules.

4. The contact-lens disinfectant according to claim 1 obtainable by a fluidized-bed process.

5. The contact-lens disinfectant according to claim 1 packed in portions of from about 10 to 200 mg in blister packs or in capsules.

6. A process for the preparation of solid active-ingredient concentrates, which comprises preparing a spray solution from sodium cumenesulphonate, methylhydroxyethylcellulose and water which is sprayed onto a mixture of magnesium perphthalate powder and sodium alkylbenzoate powder in a fluidized-bed drier at an air intake temperature of from about 60 to 80° C., and coating the granules formed with a melt of isotridecanol ethoxylate.

7. A process for the preparation of solid active-ingredient concentrates, which comprises spraying from about 70 to 90% by weight of magnesium monoperphthalate hexahydrate with an aqueous solution of from about 0.1 to 2.0% by weight of methylhydroxyethylcellulose and from about 5 to 15% by weight of sodium cumenesulphonate in a fluidized-bed drier at an air intake temperature of from about 60 to 80° C., wherein from about 3 to 10% by weight of sodium alkylbenzenesulphonate are mixed with the granules formed, and coating the mixture with a melt of from about 0.5 to 5.0% by weight of isotridecanol ethoxylate 9 EO.

8. The contact-lens disinfectant according to claim 3 wherein it is in the form of granules having a particle size of from about 50 to 500 $\mu$m.

9. The contact-lens disinfectant according to claim 5, packed in portions of from about 40 to 80 mg, in blister packs or in capsules.

* * * * *